United States Patent
Yamazaki

(10) Patent No.: US 10,722,196 B2
(45) Date of Patent: Jul. 28, 2020

(54) RADIOGRAPHIC DIAGNOSIS APPARATUS, RADIATION DETECTOR AND COLLIMATOR

(71) Applicant: CANON MEDICAL SYSTEMS CORPORATION, Otawara-shi (JP)

(72) Inventor: Masahiko Yamazaki, Utsunomiya (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 17 days.

(21) Appl. No.: 16/148,298

(22) Filed: Oct. 1, 2018

(65) Prior Publication Data

US 2019/0099139 A1    Apr. 4, 2019

(30) Foreign Application Priority Data

Oct. 2, 2017 (JP) .................................. 2017-192741
Sep. 27, 2018 (JP) .................................. 2018-181222

(51) Int. Cl.
*A61B 6/00* (2006.01)
*A61B 6/03* (2006.01)

(52) U.S. Cl.
CPC ............ *A61B 6/4291* (2013.01); *A61B 6/032* (2013.01); *A61B 6/4035* (2013.01)

(58) Field of Classification Search
CPC ...... A61B 6/032; A61B 6/4035; A61B 6/4291
See application file for complete search history.

(56) References Cited

U.S. PATENT DOCUMENTS

| 5,231,655 A * | 7/1993 | Wei ......................... G21K 1/025 378/147 |
| 6,707,884 B1 * | 3/2004 | Ogawa .................... G21K 1/025 378/154 |
| 2008/0165922 A1 | 7/2008 | Yanoff et al. |
| 2011/0019801 A1 * | 1/2011 | Eichenseer ........... G01T 1/2985 378/147 |
| 2012/0132834 A1 * | 5/2012 | Freund .................... G21K 1/025 250/505.1 |
| 2012/0219107 A1 * | 8/2012 | Kurochi ................. G21K 1/025 378/19 |
| 2013/0077738 A1 * | 3/2013 | Kreisler ................... A61B 6/03 378/7 |
| 2013/0235972 A1 * | 9/2013 | Kuroiwa ................ G21K 1/025 378/19 |
| 2015/0063531 A1 * | 3/2015 | Ikhlef .................. G01N 23/046 378/19 |

(Continued)

FOREIGN PATENT DOCUMENTS

JP    2008-168125    7/2008

*Primary Examiner* — Mark R Gaworecki
(74) *Attorney, Agent, or Firm* — Oblon, McClelland, Maier & Neustadt, L.L.P.

(57) ABSTRACT

A radiographic diagnosis apparatus according to a present embodiment includes: an X-ray source configured to generate an X-ray; an X-ray detector configured to detect the X-ray and to generate an electric signal according to the X-ray; and a collimator provided on an X-ray incident side of the X-ray detector and the collimator including an absorption wall configured to absorb a scattered X-ray. The absorption wall includes absorption portions arranged along an incident direction of the X-ray. The absorption portions are arranged at unequal intervals along the incident direction.

19 Claims, 11 Drawing Sheets

(56) References Cited

U.S. PATENT DOCUMENTS

| | | | |
|---|---|---|---|
| 2015/0179291 A1* | 6/2015 | Yu | G21K 1/025 378/4 |
| 2016/0078972 A1* | 3/2016 | Reitz | G21K 1/025 378/147 |
| 2018/0328863 A1* | 11/2018 | Rui | G01T 1/242 |

* cited by examiner

1

RADIOGRAPHIC DIAGNOSIS APPARATUS, RADIATION DETECTOR AND COLLIMATOR

CROSS-REFERENCE TO RELATED APPLICATION

This application is based upon and claims the benefit of priority from Japanese Patent Application No. 2017-192741, filed on Oct. 2, 2017, and Japanese Patent Application No. 2018-181222, filed on Sep. 27, 2018, the entire contents of each of which are incorporated herein by reference.

FIELD

Embodiments described herein relate generally to a radiographic diagnosis apparatus, a radiation detector, and a collimator.

BACKGROUND

There is known a radiographic diagnosis apparatus configured to generate a radiographic image in which body tissues of an object is imaged by irradiating the object with radiographic rays. The radiographic diagnosis apparatus is a superordinate concept that includes, e.g., an X-ray diagnostic apparatus and an X-ray CT (Computed Tomography) apparatus. The X-ray diagnostic apparatus includes an X-ray source and an X-ray detector, and generates X-ray image data projecting the internal structure of an object on the basis of X-rays detected by the X-ray detector. In addition, the X-ray CT apparatus includes an X-ray source and an X-ray detector, and generates CT image data of respective axial cross-sections of an object and/or volume data of the object on the basis of X-rays detected by the X-ray detector.

The radiographic diagnosis apparatus such as the X-ray CT apparatus includes a collimator on the X-ray incident side of the X-ray detector. The collimator removes scattered X-rays that are made incident on the X-ray detector, by absorbing scattered ray components contained in the incident X-ray to the X-ray detector, i.e., by absorbing scattered X-rays. In general, the collimator includes plural absorption walls that are arranged along the X-ray incident direction and are made of a material capable of absorbing scattered X-rays.

In addition, heavy metals such as Mo (molybdenum) and W (tungsten) are used in large quantities as the material of the absorption walls constituting the collimator. Thus, there is a problem that the manufacturing cost of the collimator is greatly increased and the weight of the collimator is greatly increased.

BRIEF DESCRIPTION OF THE DRAWINGS

In accompanying drawings.

Each of FIG. 2A

Each of FIG. 9A

DETAILED DESCRIPTION

A radiographic diagnosis apparatus, a radiation detector, and a collimator according to a present embodiment will be described by referring to the accompanying drawings.

A radiographic diagnosis apparatus according to a present embodiment includes: an X-ray source configured to generate an X-ray; an X-ray detector configured to detect the X-ray and to generate an electric signal according to the X-ray; and a collimator provided on an X-ray incident side of the X-ray detector and the collimator including an absorption wall configured to absorb a scattered X-ray. The absorption wall includes absorption portions arranged along an incident direction of the X-ray. The absorption portions are arranged at unequal intervals along the incident direction.

The radiographic diagnosis apparatus according to the present embodiment is an apparatus equipped with a collimator for removing scattered rays on the X-ray incident side of the radiation detector. The radiographic diagnosis apparatus is a superordinate concept that includes, e.g., an X-ray diagnostic apparatus and an X-ray CT apparatus. Hereinafter, a description will be given of a case where the radiographic diagnosis apparatus is an X-ray CT apparatus.

There are various methods for data acquisition methods by the X-ray CT apparatus, such as a rotate/rotate (R-R) method and a stationary/rotate (S-R) method. In the rotate/rotate method, the X-ray source and the X-ray detector integrally rotate around an object. In the stationary/rotate method, multiple detection elements are annually arrayed and only the X-ray tube is rotated around an object. The present invention can be applied to either method. Hereinafter, a description will be given of a case where the third generation rotate/rotate method currently occupying the mainstream is adopted for the radiographic diagnosis according to the present embodiment.

Figure 1:
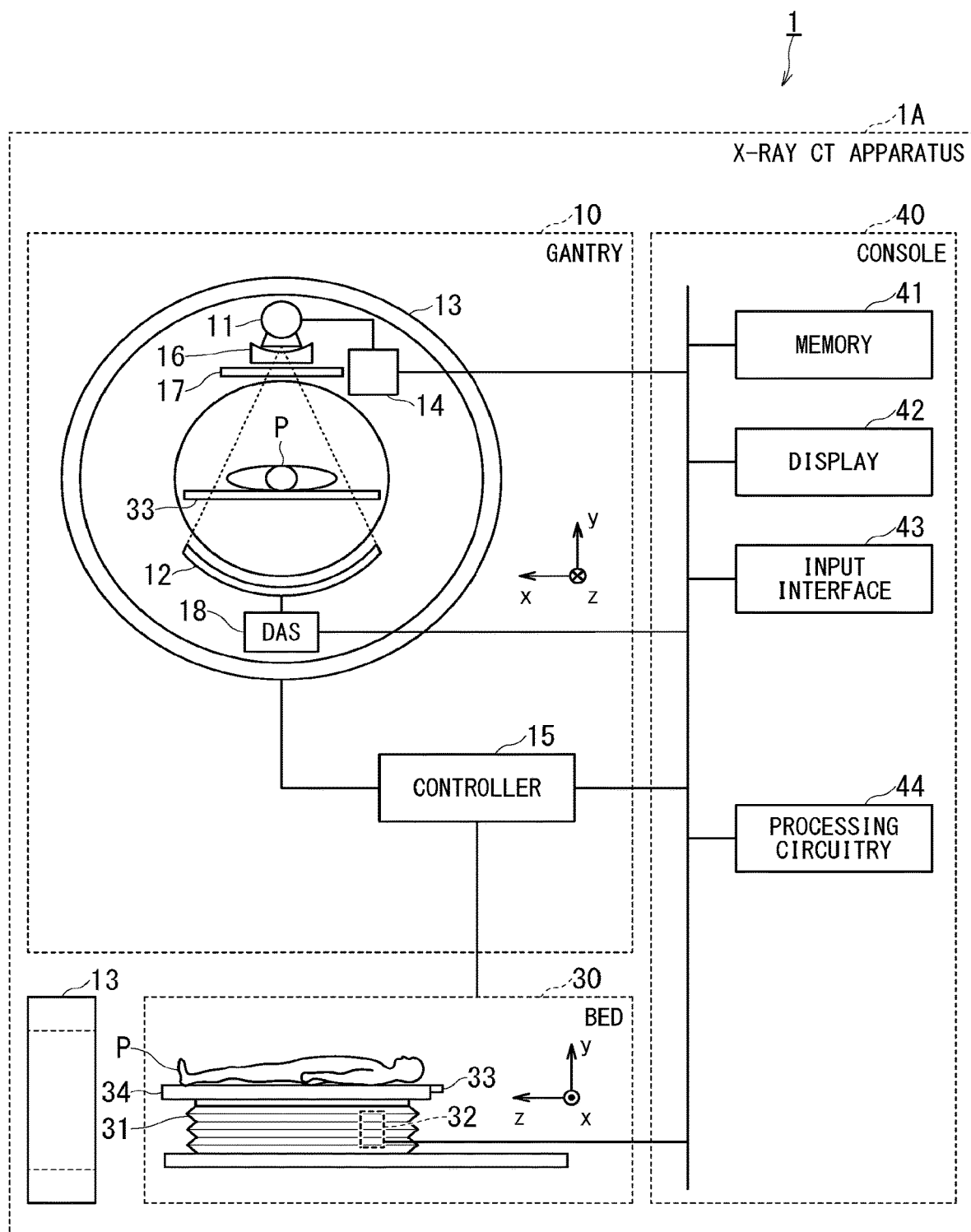
FIG. 1 is a block diagram illustrating a configuration of an X-ray CT apparatus which is one aspect of a radiographic diagnosis apparatus according to a present embodiment.

FIG. 1 is a block diagram illustrating a configuration of the X-ray CT apparatus which is one aspect of the radiographic diagnosis apparatus according to the present embodiment.

FIG. 1 shows an X-ray CT apparatus 1A which is one aspect of the radiographic diagnosis apparatus 1 according to the present embodiment. The X-ray CT apparatus 1A includes a gantry 10, a bed 30, and a console 40. The gantry 10 and the bed 30 are installed in an examination room. The gantry 10 acquires X-ray detection data related to an object (e.g., a patient) P placed on the bed 30. The console 40 is installed in a control room adjacent to the examination room, generates multidirectional projection data on the basis of multidirectional detection data, and reconstructs a CT image on the basis of the multidirectional projection data so as to display the CT image.

The gantry 10 includes an X-ray source (e.g., X-ray tube) 11, an X-ray detector 12, a rotating frame 13, an X-ray high-voltage device 14, a controller 15, a wedge 16, a diaphragm 17, a DAS (Data Acquisition System) 18, and a collimator 19 (shown in FIG. 2).

The X-ray tube 11 is provided in the rotating frame 13. The X-ray tube 11 is a vacuum tube that radiates thermoelectrons from a cathode (filament) to an anode (target) by applying high voltage supplied from the X-ray high-voltage device 14. The present embodiment can be applied to a single-tube type X-ray CT apparatus and also to a so-called multi-tube type X-ray CT apparatus in which plural pairs of an X-ray tube and an X-ray detector are mounted on a rotation ring.

Note that the X-ray source for generating X-rays is not limited to the X-ray tube 11. Instead of the X-ray tube 11, for instance, X-rays may be generated by the fifth generation system. The fifth generation system includes a focus coil for converging an electron beam generated from an electron gun, a deflection coil for electromagnetically deflecting the electron beam, and a target ring that encloses a half of the circumference of the patient P and generates X-rays by being subjected to collision of the deflected electron beam.

The X-ray detector 12 is one aspect of a radiation detector, and is provided in the rotating frame 13 so as to face the X-ray tube 11. The X-ray detector 12 detects X-rays radiated from the X-ray tube 11 and outputs detection data corresponding to X-ray dose to the DAS 18 as an electric signal. The X-ray detector 12 includes, e.g., plural X-ray detection element lines configured by arraying plural X-ray detection elements in the channel direction along one circular arc such that the focus of the X-ray tube becomes the center of the array. For instance, the X-ray detector 12 has a structure in which plural X-ray detection element lines configured by arraying plural X-ray detection elements in the channel direction are arrayed in the slice direction (i.e., row direction).

In this embodiment, the collimator 19 (shown in FIG. 2) is provided on the X-ray incident side of the X-ray detector 12. The collimator 19 is also called a grid, and absorbs scattered X-rays of incident X-rays so as to remove scattered X-rays that are made incident on the X-ray detector 12. The collimator 19 has absorption walls G and H (shown in FIG. 3 to FIG. 5) made of a material capable of absorbing scattered X-rays.

Further, the X-ray detector 12 is an indirect conversion type detector equipped with a scintillator array 51 and an optical sensor array 52 (shown in FIG. 2). The scintillator array 51 includes plural scintillators, and each scintillator has a scintillator crystal that outputs light with a photon dose corresponding to the incident X-ray dose. The photosensor array 52 has a function of converting the light outputted from the scintillator array 51 into an electric signal corresponding to the light amount from the scintillator array 51, and includes, e.g., an optical sensor such as a PMT (Photo Multiplier Tube).

The rotating frame 13 supports the X-ray tube 11 and the X-ray detector 12 such that the X-ray tube 11 and the X-ray detector 12 face each other. The rotating frame 13 is an annular frame configured to integrally rotate the X-ray tube 11 and the X-ray detector 12 under the control of the controller 15 described below. The rotating frame 13 may further include and support the X-ray high-voltage device 14 and the DAS 18, in addition to the X-ray tube 11 and the X-ray detector 12.

In this manner, the X-ray CT apparatus 1A rotates the rotating frame 13, which makes the X-ray tube 11 and the X-ray detector 12 face each other and supports both, around the patient P so as to acquire detection data for the full round of the patient P, i.e., 360° of the entire surrounding of the patient P. The CT image reconstruction method is not limited to the full scan reconstruction in which detection data for 360° are used. For instance, the X-ray CT apparatus 1A may adopt the half scan reconstruction in which a CT image is reconstructed on the basis of detection data for the half round (180°)+fan angle.

The X-ray high-voltage device 14 includes electric circuits such as a transformer and a rectifier. The X-ray high-voltage device 14 includes a non-illustrated high-voltage generator having a function of generating a high voltage applied to the X-ray tube 11 under the control of the controller 15 described below and a non-illustrated X-ray controller for controlling the output voltage according to X-rays radiated by the X-ray tube 11 under the control of the controller 15 described below. The high-voltage generator may be a transformer type or an inverter type. The X-ray high-voltage device 14 may be provided on the rotating frame 13 described below or on the fixed frame side of the gantry 10.

The controller 15 includes processing circuitry, a memory, and a driving mechanism such as a motor and an actuator. The configuration of the processing circuitry and the configuration of the memory are respectively the same as the processing circuitry 44 and the memory 41 of the console 40 to be described below, and duplicate description is omitted.

The controller 15 has a function of receiving an input signal from a non-illustrated input interface mounted on the console 40 or the gantry 10 and controlling the operation of the gantry 10 and the bed 30. For instance, on receiving the input signal, the controller 15 controls the rotation of the rotating frame 13, controls the gantry 10 so as to tilt the gantry 10, and controls the operation of the bed 30 and the table 33. The control of tilting the gantry 10 is achieved by the controller 15 that rotates the rotating frame 13 around the axis in parallel to the X-axis direction on the basis of tilt angle information inputted by the input interface mounted on the gantry 10. The controller 15 may be provided in the gantry 10 or in the console 40.

In addition, the controller 15 also controls the angle of the X-ray tube 11 and the operation of the wedge 16 and the diaphragm 17 described below, on the basis of imaging conditions inputted from the input interface mounted on the console 40 and/or the gantry 10.

The wedge 16 is provided on the rotating frame 13 so as to be disposed on the X-ray emission side of the X-ray tube 11. The wedge 16 is a filter for adjusting X-ray dose radiated from the X-ray tube 11 under the control of the controller 15. Specifically, the wedge 16 is a filter that transmits and attenuates the X-rays radiated from the X-ray tube 11 such that the X-rays radiated onto the patient P from the X-ray tube 11 have a predetermined distribution. For instance, the wedge 16 (i.e., wedge filter, bow-tie filter) is a filter obtained by processing aluminum such that the aluminum has a predetermined target angle or a predetermined thickness.

The diaphragm 17 is also called a slit and is provided in the rotating frame 13 so as to be arranged on the X-ray emission side of the X-ray tube 11. The diaphragm 17 is, e.g., a lead plate for narrowing the irradiation range of the X-rays transmitted through the wedge 16 under the control of the controller 15, and forms an X-ray irradiation opening by a combination of plural lead blades and other components.

The DAS 18 is provided in the rotating frame 13. The DAS 18 includes an amplifier that performs amplification processing on electric signals outputted from the respective X-ray detection elements of the X-ray detector 12 under the control of the controller 15, and further includes an A/D (Analog to Digital) converter for converting the electric signals into digital signals under the control of the controller 15. The DAS 18 generates detection data subjected to the amplification processing and the digital conversion. The detection data generated by the DAS 18 are transferred to the console 40.

The detection data generated by the DAS 18 are transmitted from a transmitter equipped with a light emitting diode (LED) provided on the rotating frame 13 by optical communication to a non-rotating portion of the gantry 10, e.g., a receiver equipped that is with a photodiode and id provided on a non-illustrated fixed frame, and then are transferred to the console 40. The method of transmitting the detection data from the rotating frame 13 to the non-rotating portion of the gantry 10 is not limited to the above-described optical communication, and any method may be adopted as long as it is non-contact type data transmission. The non-illustrated fixed frame is a frame that rotatably supports the rotating frame 13.

The bed 30 includes a base 31, a bed driving device 32, a table 33, and a support frame 34. The bed 30 is a device for placing the patient P to be scanned and moving the patient P under the control of the controller 15.

The base 31 is a housing that supports the support frame 34 movably in the vertical direction (i.e., y-axis direction). The bed driving device 32 is a motor or an actuator that moves the table 33 with the object P is placed thereon in the longitudinal direction (i.e., z-axis direction) of the table 33. The table 33 provided on the upper surface of the support frame 34 is a plate having a shape capable of placing the patient P.

In addition to the table 33, the bed driving device 32 may move the support frame 34 in the longitudinal direction (i.e., z-axis direction) of the table 33. In addition, the bed driving device 32 may move the table 34 together with the base 31 of the bed 30. When the present invention is applied to the standing CT (i.e., CT in a standing position), it may be a method of moving the patient-moving-mechanism corresponding to the table 33. In the case of executing imaging that involves relative change of positional relationship between the table 33 and the imaging system of the gantry 10 such as helical scan imaging and scanogram imaging for positioning, the relative change of the positional relationship may be performed by driving the table 33, running the fixed frame of the gantry 10, or a combination of both.

In the present embodiment, the rotation axis of the rotating frame 13 in the non-tilted state or the longitudinal direction of the table 33 of the bed 30 is defined as the z-axis direction, the axial direction orthogonal to the z-axis direction and horizontal to the floor surface is defined as the x-axis direction, and the axial direction orthogonal to the z-axis direction and perpendicular to the floor surface is defined as the y-axis direction.

The console 40 includes a memory 41, a display 42, an input interface 43, and processing circuitry 44. In the following description, it is assumed that the console 40 executes all the functions with a single console, but these functions may be executed by plural consoles.

The memory 41 has a configuration including a recording medium readable by a processor. The recording medium is, e.g., a RAM (Random Access Memory), a semiconductor memory element such as a flash memory, a hard disk, and an optical disk.

Detection data generated by the X-ray CT apparatus 1A may be stored in the memory 41, and the same holds true for projection data and reconstructed image data that are generated by the X-ray CT apparatus 1A as described below. The detection data, the projection data, and the reconstructed image data generated by the X-ray CT apparatus 1A may be stored in an external storage device such as an image server that can be connected to the X-ray CT apparatus 1A via a network such as a LAN (Local Area Network). Similarly, a part or all of the programs and data in the recording medium of the memory 41 may be downloaded by communication via a network or may be given to the memory 41 via a portable recording medium such as an optical disc.

The display 42 displays various types of information. For instance, the display 42 outputs a medical image (CT image) generated by the processing circuitry 44 and/or a GUI (Graphical User Interface) for receiving various operations from a user. The display 42 is, e.g., a liquid crystal display, a CRT (Cathode Ray Tube) display, or an OLED (Organic Light Emitting Diode) display.

The input interface 43 receives various input operations from a user, converts the received input operations into electric signals, and outputs the electric signals to the processing circuitry 44. For instance, the input interface 43 receives, from a user, setting information such as imaging conditions for acquiring data, reconstruction conditions for reconstructing a CT image, image processing conditions for performing image processing on the CT image. The input interface 43 is realized by, e.g., an input device such as a mouse, a keyboard, a track ball, a switch, a button, and a joystick.

The processing circuitry 44 is a processor that controls the entire operation of the X-ray CT apparatus 1A by reading out and executing the programs stored in the memory 41. The processing circuitry 44 performs preprocessing such as correction processing on the detection data outputted from the DAS 18 so as to generate projection data. In addition, the processing circuitry 44 reconstructs the projection data so as to generate CT image data of axial cross-sections. Further, the processing circuitry 44 generates volume data on the basis of the CT image data so as to generate, as CT image data, image data of an arbitrary cross-section (MPR: Multi-Planar Reconstruction) and projection image data viewed from an arbitrary direction. The volume data are data that include distribution information of CT values in three-dimensional space. The projection image data are obtained by performing volume rendering processing on the volume data or by performing surface rendering processing on the volume data.

Next, a description will be given of the structure of the collimator 19 included in the X-ray CT apparatus 1A according to the present embodiment in detail.

Figure 2A:
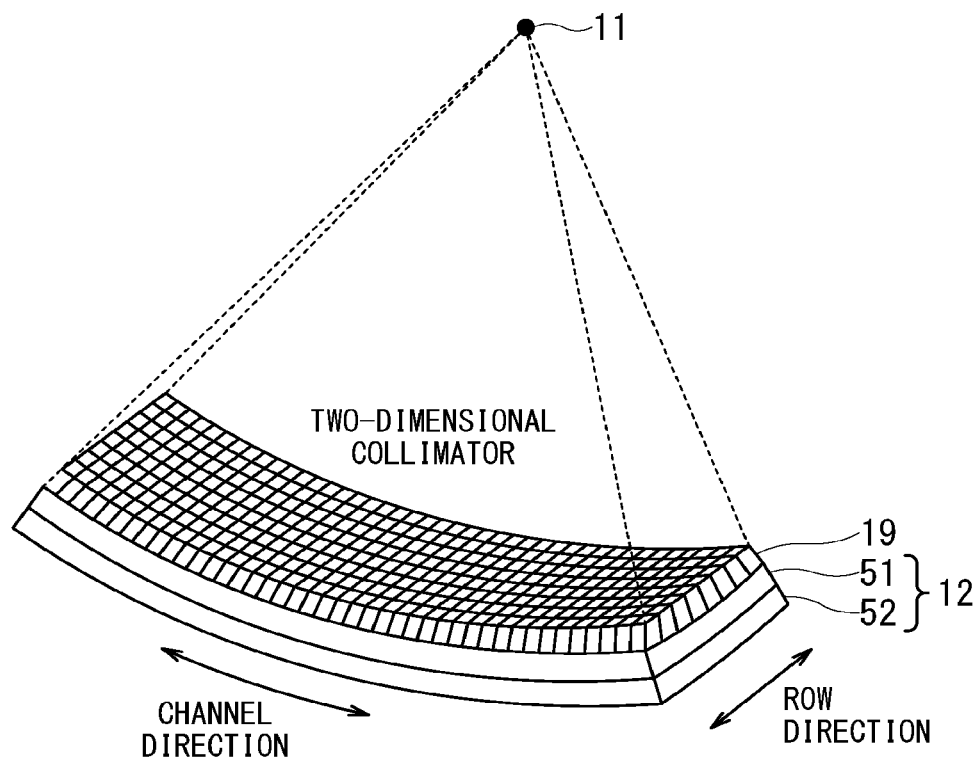
FIG. 2B is a perspective view illustrating an appearance of a collimator according to a present embodiment.
Figure 2B:
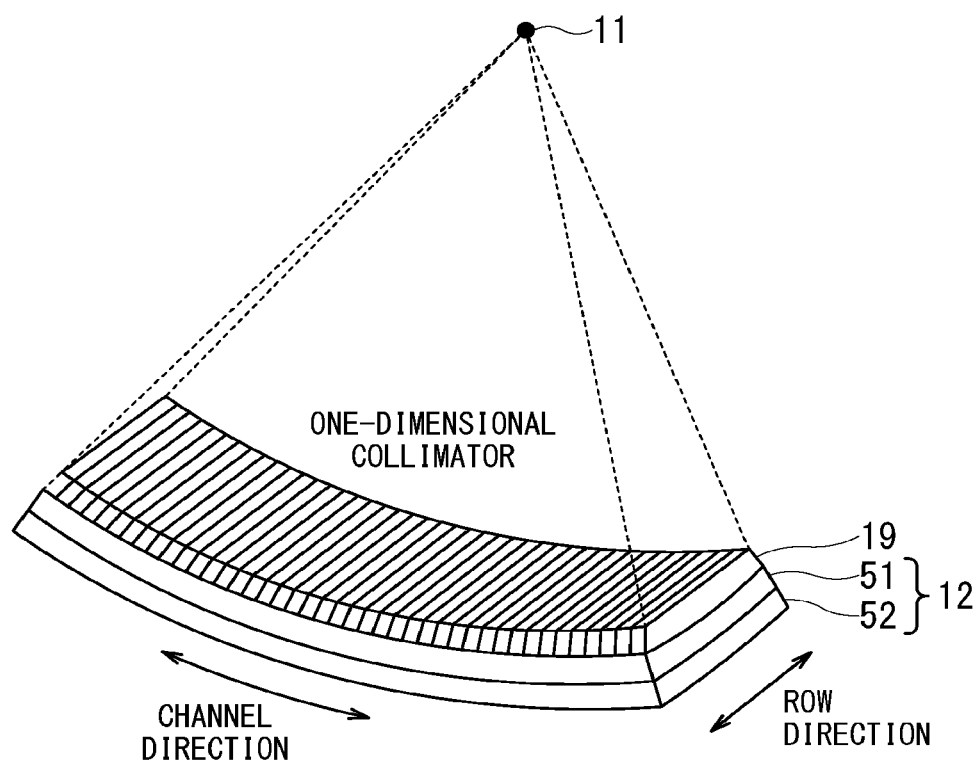

Each of FIG. 2A and FIG. 2B is a perspective view illustrating an appearance of the collimator 19.

As shown in FIG. 2A and FIG. 2B, the collimator 19 is arranged on the X-ray incident side of the X-ray detector 12. FIG. 2A shows a collimator including plural absorption walls each extending in the row direction and arranged along the channel direction, and including plural absorption walls each extending in the channel direction and arranged along the row direction, i.e., a two-dimensional collimator. FIG. 2B shows a collimator including only plural absorption walls each extending in the row direction and arranged along the channel direction, i.e., a one-dimensional collimator. Although the collimator 19 according to the present embodiment can be applied to both of the one-dimensional collimator and the two-dimensional collimator, in the following, a description will be given of the case of the one-dimensional collimator shown in FIG. 2B.

Figure 3:
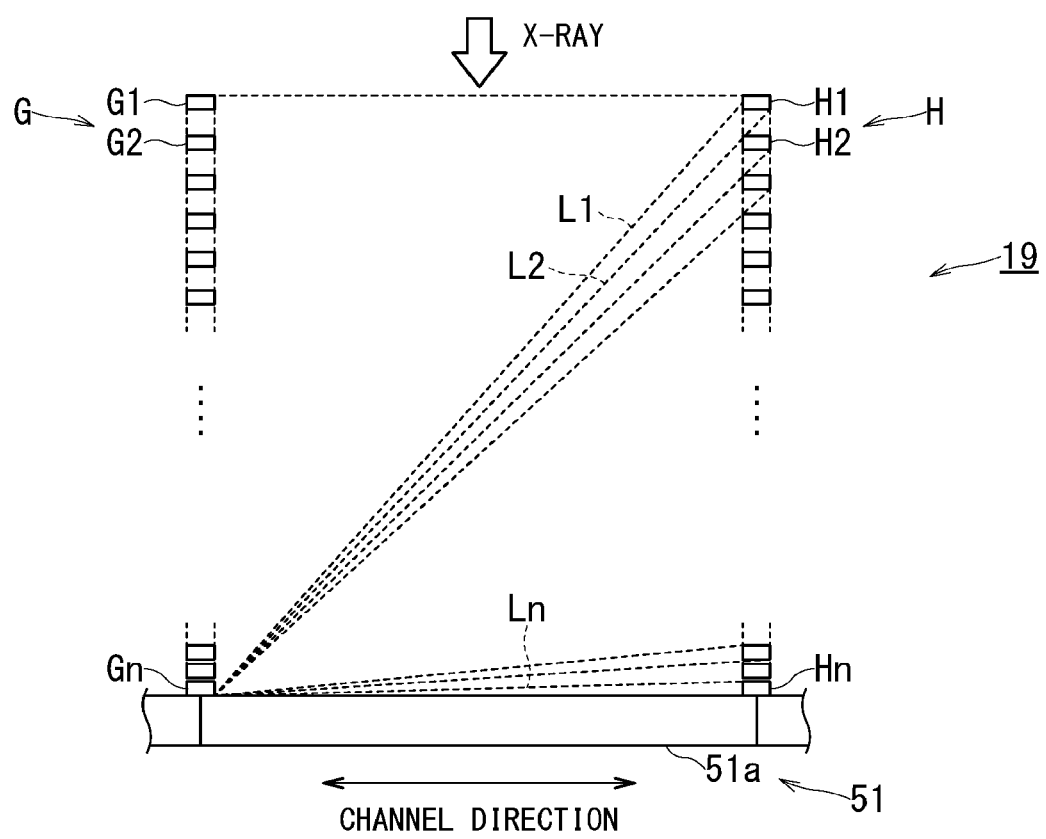
FIG. 3 is a front view illustrating a first aspect of a structure of the collimator according to the present embodiment.

FIG. 3 is a front view illustrating the first aspect of the structure of the collimator 19.

As shown in FIG. 3, the collimator 19 is provided on the X-ray incident side of the scintillator array 51. The scintillator array 51 includes elements 51a (corresponding to the X-ray detecting element) in the channel direction. Additionally, the collimator 19 arranges plural absorption walls along the channel direction so as to separate the plural elements 51a in the channel direction. Each absorption wall is arranged such that a side surface thereof is along the X-ray incident direction. Each absorption wall absorbs scattered rays. FIG. 3 shows two absorption walls G and H adjacent to each other in the channel direction among the plural absorption walls.

Assuming that n is an integer of 3 or more, the absorption wall G includes n absorption portions G1 to Gn arranged along the X-ray incident direction and non-absorption portions between the respective absorption portions G1 to Gn. The absorption wall H adjacent to the absorption wall G in the channel direction includes n absorption portions H1 to Hn arranged along the X-ray incident direction. The n absorption portions G1 to Gn have intervals (pitches) therebetween and are arranged at unequal intervals along the X-ray incident direction. Between each of the n absorption portions G1 to Gn, a permeable member such as an adhesive is disposed as a non-absorption portion that transmits X-rays. The same structure as the n absorption portions G1 to Gn holds true for the n absorption portions H1 to Hn.

In the case of FIG. 3, the n absorption portions G1 to Gn provided in the absorption wall G of the collimator 19 are arranged along the X-ray incident direction at intervals such that at least the primary X-rays to be incident on the scintillator array 51 are removed. In order to remove the primary X-rays, the n absorption portions G1 to Gn are arranged in such a manner that the interval gradually decreases from the absorption portion G1 toward the absorption portion Gn. In other words, the n absorption portions G1 to Gn are disposed so as to be sparse on the side close to the X-ray tube 11 in the X-ray incident direction as compared with the side close to the scintillator array 51 in the X-ray incident direction.

Since the plural absorption portions G1 to Gn provided in the absorption wall G have such an arrangement, it is possible to absorb the primary X-rays L1 to Ln passing through the gaps (i.e., non-absorption portions) formed by the respective intervals of the n absorption portions H1 to Hn arranged in the absorption wall H, which is adjacent to the absorption wall G, without leaking. Further, by arranging the plural absorption portions G1 to Gn of the absorption wall G in this manner, it is possible to reduce the use of materials such as molybdenum and tungsten to about 10% of a conventional collimator equipped with absorption walls in which any gap is not formed. In addition to the absorption wall G, the plural absorption portions of the other absorption walls provided in the channel direction can also be arranged in the same manner as the absorption wall G.

It is not necessarily required that all of the plural absorption walls provided in the channel direction have the same arrangement. For instance, when the absorption wall H shown in FIG. 3 corresponds to the end portion among the plural absorption walls in the channel direction, the primary X-ray Ln from the outside may reach the absorption wall G in some cases. When another absorption wall exists on the right side of the absorption wall H shown in FIG. 3 among the plural absorption walls in the channel direction, the primary X-ray Ln is absorbed by this absorption wall on the right side of the absorption wall H or by the absorption wall H and does not reach the absorption wall G. Thus, as to the plural absorption walls in the channel direction, length and/or number of intervals of the plural absorption portions can be changed depending on the position of each absorption wall in the channel direction.

According to the structure of the collimator 19 shown in FIG. 3, it is possible to suppress the manufacturing cost and weight of the collimator while maintaining the function of removing scattered X-rays.

Figure 4:
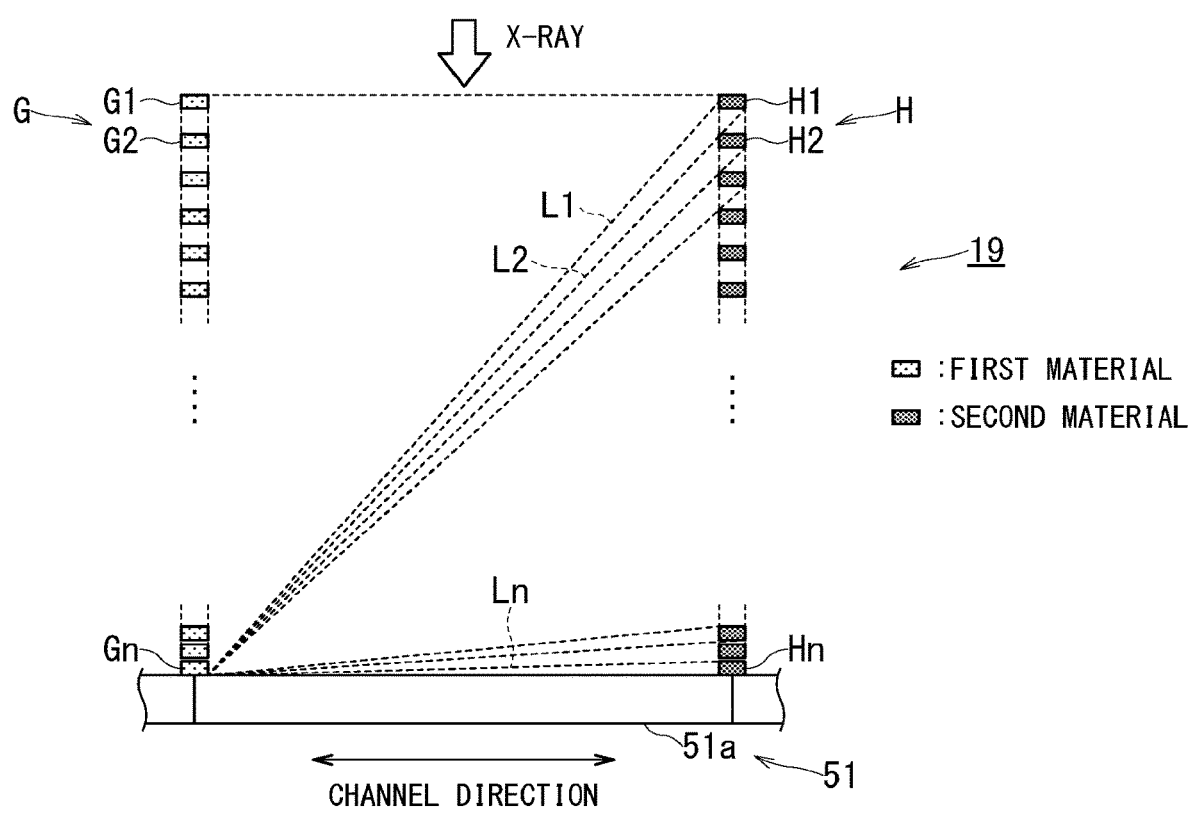
FIG. 4 is a front view illustrating a second aspect of a structure of the collimator according to the present embodiment.
Figure 5:
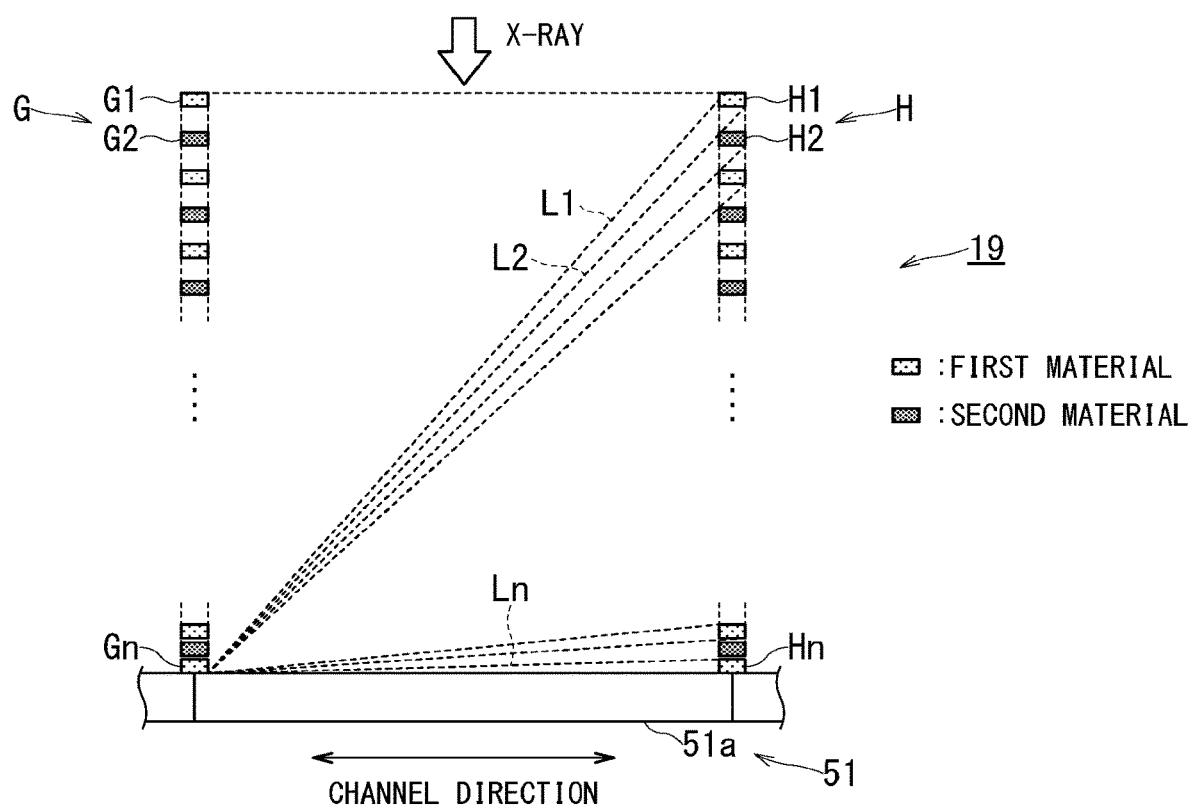
FIG. 5 is a front view illustrating a third aspect of a structure of the collimator according to the present embodiment.
Figure 6:
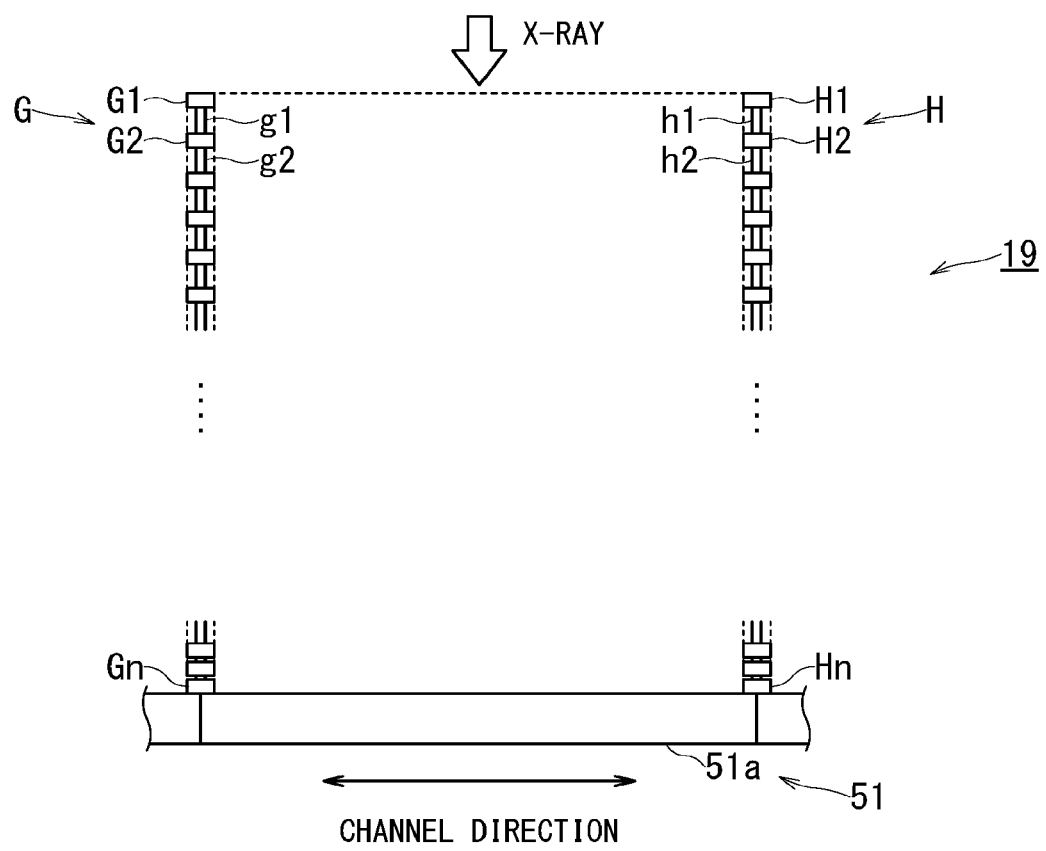
FIG. 6 is a front view illustrating a fourth aspect of a structure of the collimator according to the present embodiment.

The structure of the collimator 19 shown in FIG. 3 may be partially modified. For instance, in order to improve the absorption rate of secondary X-rays from the absorption walls, the material of the absorption walls may be changed along the channel direction as shown in FIG. 4 or the material of the plural absorption portions may be changed along the X-ray incident direction as shown in FIG. 5 or the thickness of each absorption wall may be changed (uneven) along the X-ray incident direction as shown in FIG. 6. This enables the second material to absorb the secondary X-rays that are emitted by the first material and have energy smaller than the energy of characteristic X-rays having relatively high intensity, so that the absorption rate of the secondary X-rays can be improved.

FIG. 4 is a front view illustrating the second aspect of the structure of the collimator 19.

In the collimator 19 shown in FIG. 4, the structure of the plural absorption portions having the intervals shown in FIG. 3 is adopted and the material of the absorption portions is changed along the channel direction. For instance, in the collimator 19, the first material (e.g., molybdenum) can be used for the material of the n absorption portions G1 to Gn arranged in the absorption wall G and the second material (e.g., tungsten) can be used for the material of the n absorption portions H1 to Hn arranged in the absorption wall H.

In the collimator 19 shown in FIG. 4, different materials may be used for the respective absorption walls that are adjacent to each other in the channel direction (as to the adjacent aspect, there is a case where one absorption wall and another absorption wall are adjacent to each other, and there is another case where a set of plural absorption walls and another set of plural absorption walls are adjacent to each other). For instance, in the case of using two types of materials, it is preferable that materials of plural absorption walls arranged along the channel direction are alternately changed. Additionally, for instance, in the case of using three types of materials, it is preferable that materials of plural absorption walls arranged along the channel direction are sequentially changed.

According to the second aspect of the collimator 19 shown in FIG. 4, it is possible to obtain the effect of improving the absorption rate of the secondary X-rays, in addition to the effect of the first aspect of the collimator 19 shown in FIG. 3.

FIG. 5 is a front view illustrating the third aspect of the structure of the collimator 19.

In the collimator 19 shown in FIG. 5, the structure of the plural absorption portions having the intervals shown in FIG. 3 is adopted and the respective materials of the plural absorption portions of each absorption wall are changed along the X-ray incident direction. For instance, in the collimator 19, the first material (e.g., molybdenum) can be used for the material of the absorption portions G1, G3, . . . disposed in the absorption wall G and the material of the absorption portions H1, H3, . . . disposed in the absorption wall H, and the second material (e.g., tungsten) can be used for the material of the absorption portions G2, G4, . . . disposed in the absorption wall G and the material of the absorption portions H2, H4, . . . disposed in the absorption wall H.

In the collimator 19 shown in FIG. 5, different materials may be used for the respective absorption walls that are adjacent to each other in the X-ray incident direction (as to the adjacent aspect, there is a case where one absorption wall and another absorption wall are adjacent to each other, and there is another case where a set of plural absorption walls and another set of plural absorption walls are adjacent to each other). For instance, in the case of using two types of materials, it is preferable that materials of the plural absorption walls arranged along the X-ray incident direction are alternately changed. Additionally, for instance, in the case of using three types of materials, it is preferable that materials of the plural absorption walls arranged along the X-ray incident direction are sequentially changed. Although plural different materials are used in a regular order and in the same order for the respective absorption walls such that the materials are different between any two adjacent absorption walls, plural different materials may be used in different orders for the respective absorption walls.

According to the third aspect of the collimator 19 shown in FIG. 5, it is possible to obtain the effect of improving the absorption rate of the secondary X-rays, in addition to the effect of the first aspect of the collimator 19 shown in FIG. 3.

FIG. 6 is a front view illustrating the fourth aspect of the structure of the collimator 19.

In the collimator 19 shown in FIG. 6, the structure of the plural absorption portions having the intervals shown in FIG. 3 is adopted and an absorption portion thinner than the absorption portions in the channel direction is arranged between adjacent absorption portions in the X-ray incident direction, the thinner absorption portion having the same material as the absorption portions. That is, the non-absorption portion between the absorption portions adjacent in the X-ray incident direction shown in FIG. 3 is replaced with the thinner absorption portion.

For example, the collimator 19 arranges an absorption portion g1 thinner than the absorption portion Gn in the channel direction between the absorption portions G1 and G2 arranged in the absorption wall G. For example, the collimator 19 arranges an absorption portion h1 thinner than the absorption portion Hn in the channel direction between the absorption portions H1 and H2 arranged in the absorption wall H. Note that the thinner absorption portion is not limited to the case where it is thinner than the absorption portion Gn in the channel direction. The thinner absorption portion is thinner than the absorption portion Gn in the row direction, or the thinner absorption portion is thinner than the absorption portion Gn in the channel and row directions.

According to the fourth aspect of the collimator 19 shown in FIG. 6, the non-absorption portion, that is, the adhesive layer is not required, in addition to the effect of the first aspect of the collimator 19 shown in FIG. 3.

Figure 7:
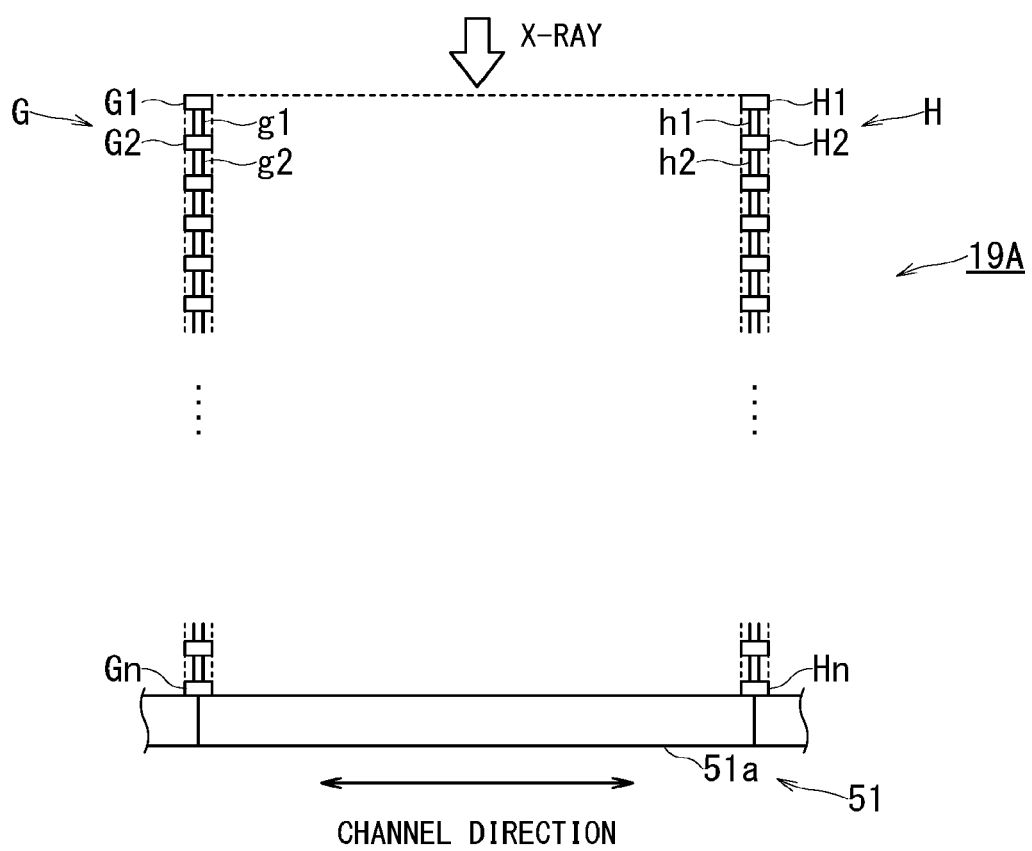
FIG. 7 is a front view illustrating a fifth aspect of a structure of the collimator according to the present embodiment.

Further, in a collimator 19A in which plural absorption portions of each absorption wall are arranged at equal intervals, an absorption portion thinner than the absorption portions in the channel direction is arranged between adjacent absorption portions in the X-ray incident direction, the thinner absorption portion having the same material as the absorption portions. This case is shown in FIG. 7. FIG. 7 shows a modified example of FIG. 6. With such a configuration, similar to the effect described above with reference to FIG. 6, the non-absorption portion, that is, the adhesive layer is not required.

Subsequently, a structure of the absorption walls of the collimator 19 shown in FIG. 3 to FIG. 6 as viewed from the side will be described with reference to FIG. 8 and FIG. 9B. For a structure of the absorption wall of the collimator 19A shown in FIG. 7, the technical concept shown in FIG. 8 and FIG. 9B can be applied.

Figure 8:
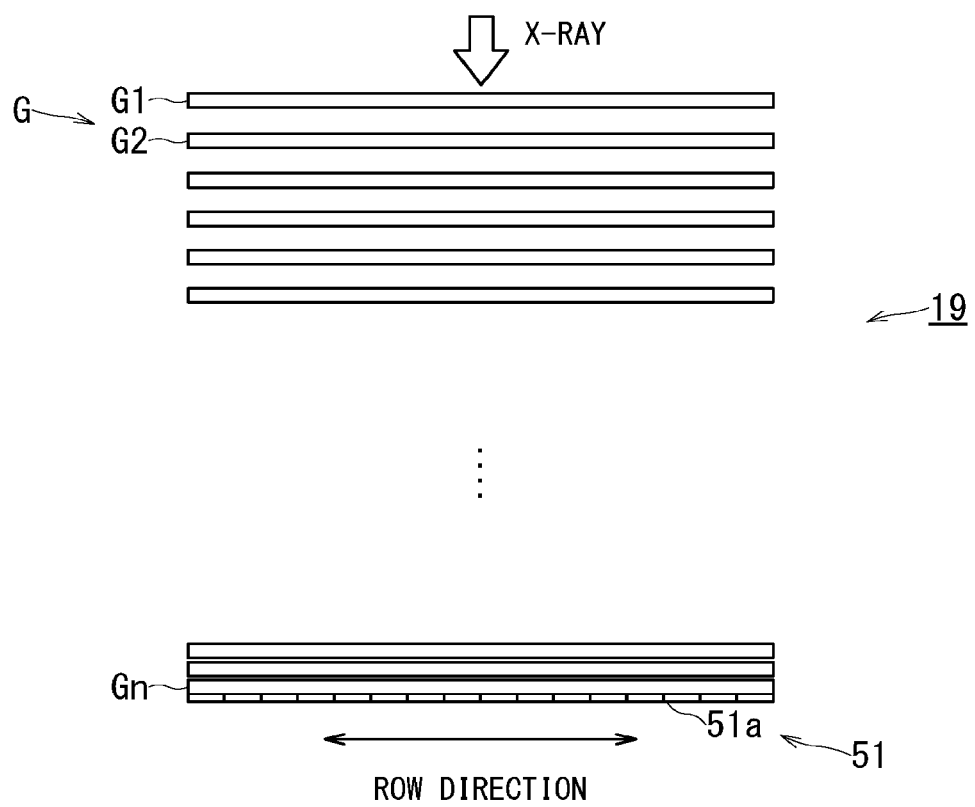
FIG. 8 is a side view illustrating a structure of the collimator according to the present embodiment.

FIG. 8 is a side view illustrating the structure of the collimator 19.

With reference to FIG. 8, the structure of the absorption wall in the row direction of the collimator 19 shown in FIG. 3 will be described. The structure of the absorption wall in the row direction of the collimator 19 shown in FIG. 4 to FIG. 6 is similar to FIG. 3.

As shown in FIG. 8, the collimator 19 arranges the absorption wall so as to straddle the plural elements 51a in the row direction. FIG. 8 shows the absorption wall G shown in FIG. 3. As described with reference to FIG. 3, the n absorption portions G1 to Gn are disposed in such a manner that the number of absorption portions is sparse on a side close to the X-ray tube 11 in the X-ray incident direction as compared with a side close to the scintillator array 51.

Figure 9A:
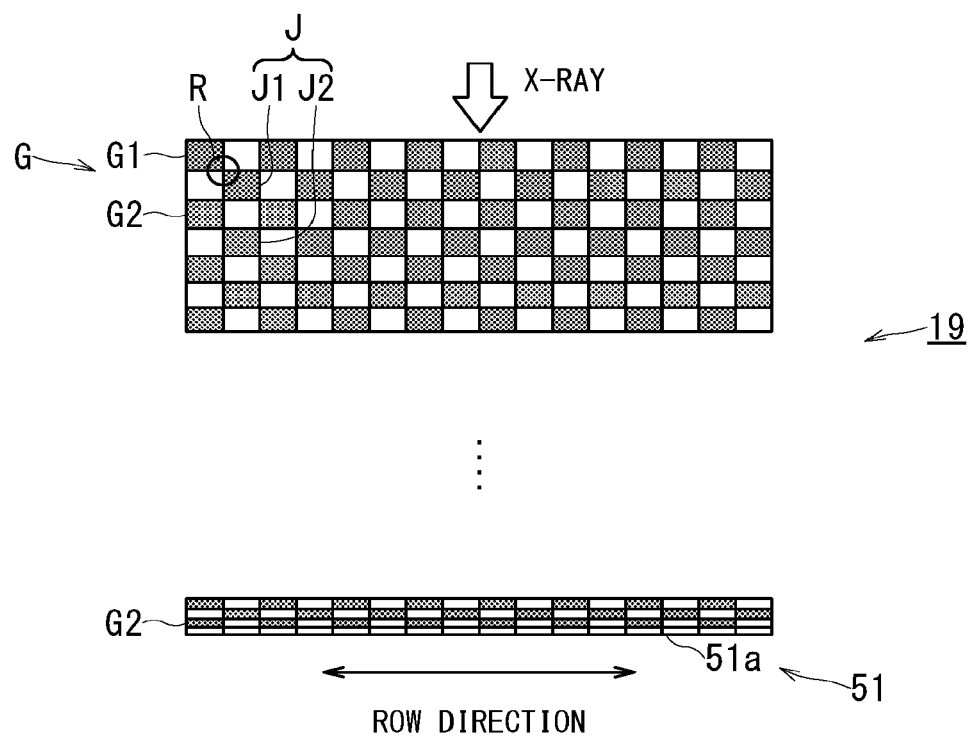
FIG. 9B is a side view illustrating a structure of the collimator according to the present embodiment.
Figure 9B:
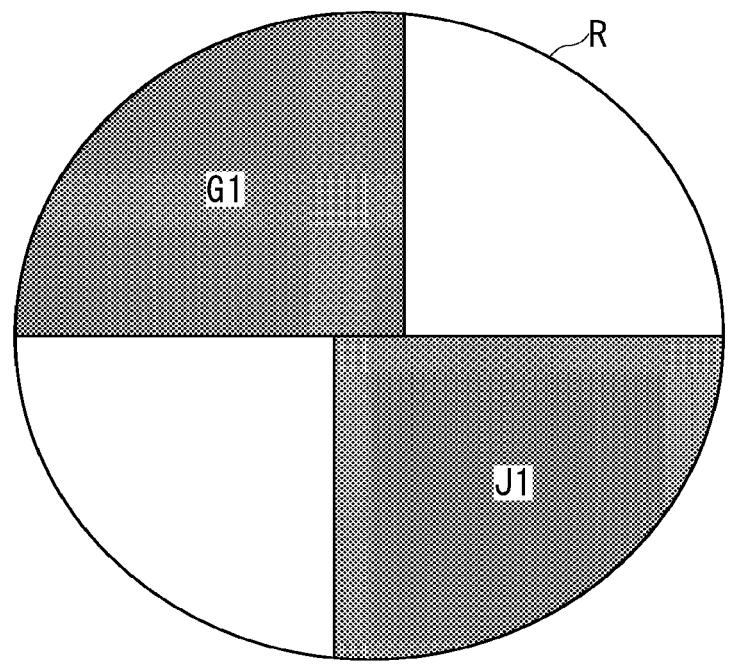

Each of FIG. 9A and FIG. 9B is a side view illustrating the structure of the collimator 19. FIG. 9B is an enlarged view of a region R shown in FIG. 9A.

With reference to FIG. 9A and FIG. 9B, the structure of the absorption wall in the row direction of the collimator 19 shown in FIG. 3 will be described. The structure of the absorption wall in the row direction of the collimator 19 shown in FIG. 4 to FIG. 6 is similar to FIG. 3.

As shown in FIG. 9A, the collimator 19 arranges plural absorption walls along the low direction so as to separate the plural elements 51a in the row direction. Further, the collimator 19 arranges plural absorption walls so that the order of the absorption portion and the non-absorption portion alternates along the row direction. For example, the order of each of the absorption portions G1, G2, . . . and the non-absorption portion of the absorption wall G, and the order of each of the absorption portions J1, J2, . . . and the non-absorption portion of the adjacent absorption wall J are alternated.

As shown in FIG. 9B, the absorption portion G1 of the absorption wall G is configured to be supported by the absorption portion J1 of the absorption wall J adjacent in the row direction. With such a configuration, it is possible to easily make each absorption wall of the collimator 19 using a 3D printer or the like.

Figure 10:
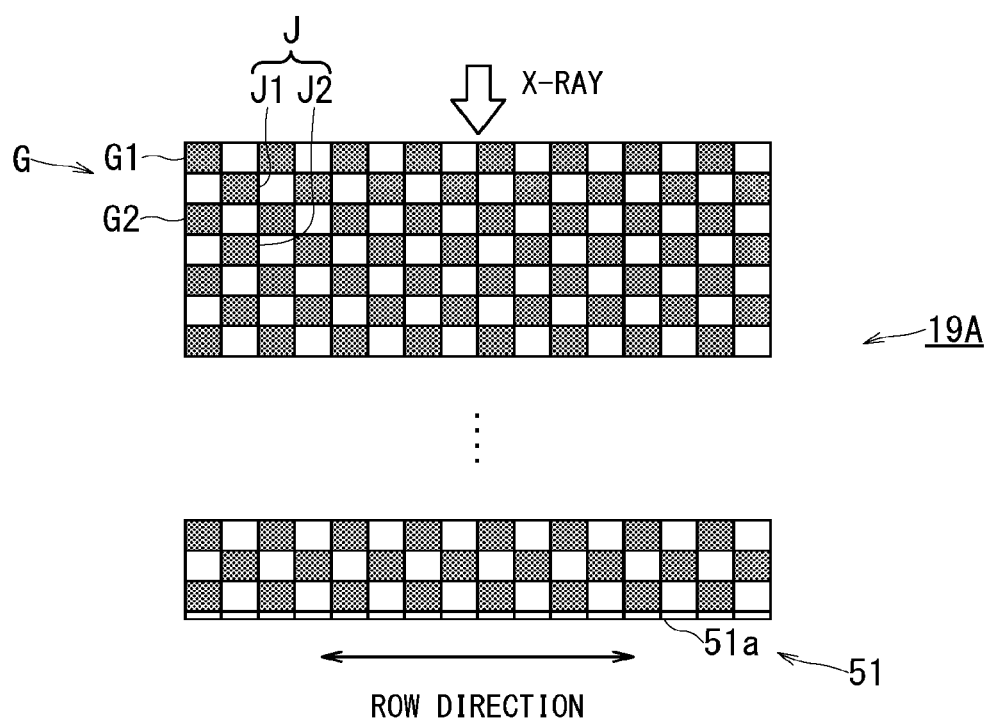
FIG. 10 is a side view illustrating a structure of the collimator according to the present embodiment; and Each of FIG. 11A

Note that the structure in the row direction of the collimator 19 in which the plural absorbing portions of each absorption wall are at unequal intervals has been described with reference to FIG. 9A and FIG. 9B. However, it is not limited to that case. In a collimator 19A (for example, the collimator 19A shown in FIG. 7) in which plural absorption portions of each absorption wall are arranged at equal intervals, there are cases where plural absorption walls are arranged so that the order of the absorption portion and the non-absorption portion alternates along the row direction. This case is shown in FIG. 10. FIG. 10 shows a modified example of FIG. 9A. Also in the collimator 19A shown in FIG. 10, the absorption portion G1 of the absorption wall G is configured to be supported by the absorption portion J1 of the absorbing wall J adjacent to the absorbing wall G, as shown in FIG. 9B. With such a configuration, similar to the effect described above with reference to FIG. 9A and FIG. 9B, it is possible to easily make each absorption wall of the collimator 19 using a 3D printer or the like.

Although a description has been given for the structure of the one-dimensional collimator (shown in FIG. 2B) in which plural absorption walls are arranged along the channel direction so far, the above-described technical idea can also be applied to the two-dimensional collimator (shown in FIG. 2A) in which plural absorption walls are arranged along the channel direction and in the row direction. In the case of the two-dimensional collimator, only plural absorption walls arranged in the row direction may be arranged as shown in any one of FIG. 3 to FIG. 7 (this includes any one of FIG. 3 to FIG. 7 combined with any one of FIG. 8 to FIG. 10). Additionally or alternatively, in the case of the two-dimensional collimator, both of the plural absorption walls arranged in the channel direction and the plural absorption walls arranged in the row direction may be arranged as shown in any one of FIG. 3 to FIG. 7 (this includes any one of FIG. 3 to FIG. 7 combined with any one of FIG. 8 to FIG. 10).

Further, as an example in which plural absorption portions of each absorption wall are arranged at unequal intervals along the X-ray incidence direction, the structure in which the intervals between the plural absorption portions widens or narrows with regularity has been described. However, it is not limited to that case. Referring to FIG. 3, when considering that the scintillator array 51 has a large number of elements 51a (corresponding to the X-ray detecting elements) in the channel direction, there is no need to provide an absorption portion on the lower side of each absorption wall. Specifically, scattered X-rays which are going to enter the detection surface of the element 51a of the scintillator array 51 at an acute angle from the absorption wall H side are absorbed by absorption walls farther from the absorption wall H (absorption walls on the right side of the absorption wall H in FIG. 3). Therefore, in the absorption wall H, it is unnecessary to dispose the absorption portion at the incident position of the scattered X-rays.

Figure 11A:
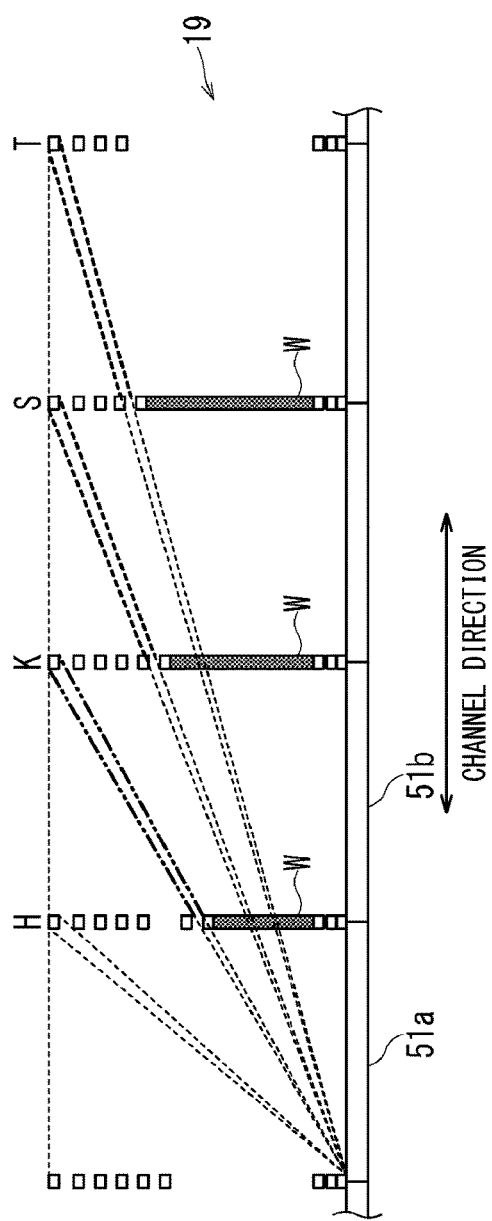
FIG. 11B is a front view illustrating a sixth aspect of a structure of the collimator according to the present embodiment.
Figure 11B:
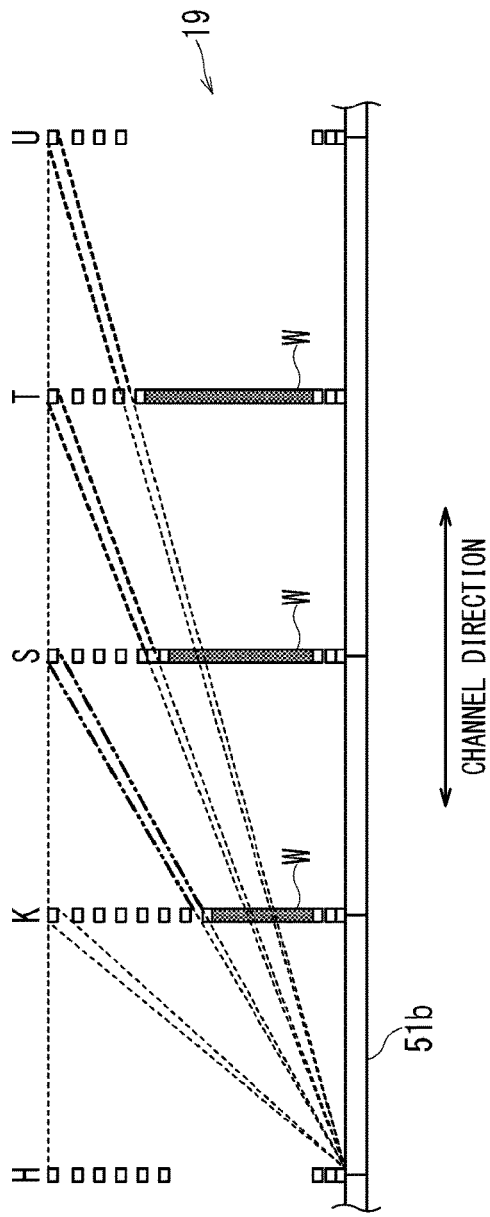

Each of FIG. 11A and FIG. 11B is a front view illustrating the sixth aspect of the structure of the collimator 19.

FIG. 11A shows scattering X-rays which are taken into consideration when element 51a in scintillator array 51 is used as a reference, the scattering X-rays entering from the right side of the element 51a. The absorption wall H arranges the absorption portion at a position which absorbs scattered X-rays (two-dotted broken line in FIG. 11A) not absorbed by the adjacent absorption wall K.

Scattered rays which are going to enter at an acute angle with respect to the detection surface of the element 51a are absorbed by the absorption walls K, S, . . . farther than the absorption wall H (thick broken lines in FIG. 11A). Therefore, in the absorption wall H, it is unnecessary to dispose the absorption portion on the lower side W where extension lines of the scattered X-rays collide. Likewise, with respect to the absorption walls K, S, . . . , it is unnecessary to arrange the absorption portion on the lower side W.

From FIG. 11A, it is found that, for the absorption wall H close to the reference element 51a, it is necessary to dispose a large number of absorption portions on the lower side, and the necessary absorption portion decreases as the distance from the element 51a increases. In FIG. 11A, only the right side of the reference element 51a is illustrated, but the same applies to the left side of the element 51a.

FIG. 11B shows scattering X-rays which are taken into consideration when element 51b in scintillator array 51 is used as a reference, the scattering X-rays entering from the right side of the element 51a. The element 51b is adjacent to the element 51a in FIG. 11A. The absorption wall K arranges the absorption portion at a position which absorbs scattered X-rays (two-dotted broken line in FIG. 11B) not absorbed by the adjacent absorption wall S.

Scattered rays which are going to enter at an acute angle with respect to the detection surface of the element 51b are absorbed by the absorption walls S, T, . . . farther than the absorption wall K (thick broken lines in FIG. 11B). Therefore, in the absorption wall K, it is unnecessary to dispose the absorption portion on the lower side W where extension lines of the scattered X-rays collide. Likewise, with respect to the absorption walls S, T, . . . , it is unnecessary to arrange the absorption portion on the lower side W.

From FIG. 11B, it is found that, for the absorption wall K close to the reference element 51b, it is necessary to dispose a large number of absorption portions on the lower side, and the necessary absorption portion decreases as the distance from the element 51b increases. In FIG. 11B, only the right side of the reference element 51b is illustrated, but the same applies to the left side of the element 51b.

Then, the position of the absorption portion necessary for each absorption wall is obtained while shifting the reference element as 51a, 52b, . . . . The position of absorption portion necessary for each absorption wall is calculated by integrating the positions of the absorption portions in all the reference elements.

With this configuration, the installation of the absorption portion can be greatly omitted for the lower side of the absorption wall. In particular, the installation of the absorption portion can be greatly omitted on the end side in the channel direction compared with the center of the collimator 19.

According to at least one embodiment described above, it is possible to suppress the manufacturing cost and weight of the collimator.

In the above-described embodiment, the term "processor" may refer to a dedicated or general purpose CPU (Central Processing Unit) and a GPU (Graphics Processing Unit), or refer to an application specific Integrated Circuit (ASIC), a circuit such as a programmable logic device or the like. The programmable logic device includes, for example, a Simple Programmable Logic Device (SPLD), a Complex Programmable Logic Device (CPLD), and a Field Programmable Gate Array (FPGA). The processor realizes various functions by reading out and executing the program stored in the storage medium.

In the above-described embodiment, an example where the single processor of the processing circuitry realizes each function has been described, but the present invention is not limited to that case. The processing circuitry may be configured by combining independent processors, and each processor may realize each function. In the case where processors are provided, the storage medium for storing the program may be provided for each processor individually, or one storage medium may collectively store programs corresponding to the functions.

In the above-described embodiment, the case where the integration of the scintillator array 51 and the optical sensor array 52 is referred to as "radiation detector" and "X-ray detector" has been described. However, the integration of the collimator 19, the scintillator array 51, and the optical sensor array 52 may be referred to as "radiation detector" and "X-ray detector" in some cases.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A radiographic diagnosis apparatus comprising:
   an X-ray source configured to generate an X-ray;
   an X-ray detector configured to detect the X-ray and to generate an electric signal according to the X-ray; and
   a collimator provided on an X-ray incident side of the X-ray detector and the collimator including an absorption wall configured to absorb a scattered X-ray, wherein
   the absorption wall includes absorption portions arranged along an incident direction of the X-ray, and
   the absorption portions are arranged at unequal intervals along the incident direction.

2. The radiographic diagnosis apparatus according to claim 1, wherein
   the absorption portions are disposed in such a manner that a number of absorption portions is sparse on a side close to the X-ray source in the incident direction as compared with a side close to the X-ray detector.

3. The radiographic diagnosis apparatus according to claim 1, wherein
   a permeable member configured to transmit the X-ray is disposed between the absorption portions.

4. The radiographic diagnosis apparatus according to claim 1, further comprising:
   a thinner absorption portion which is thinner than the absorption portions, the thinner portion being the same material as the absorption portions and being arranged between the absorption portions.

5. The radiographic diagnosis apparatus according to claim 1, wherein
   two directions in which detection elements are able to be arranged in the X-ray detector are defined as a row direction and a channel direction,
   the absorption wall comprises absorption wall elements, each of the absorption wall elements extends in the row direction, and
   the absorption wall elements are arranged along the channel direction.

6. The radiographic diagnosis apparatus according to claim 5, wherein
   materials of the absorption wall elements arranged along the channel direction are changed along the channel direction.

7. The radiographic diagnosis apparatus according to claim 5, wherein
   the absorption wall has a configuration in which an order of each of the absorption portions and a non-absorption portions is alternated along the row direction.

8. The radiographic diagnosis apparatus according to claim 7, wherein
   the absorption wall includes a first absorption wall element and a second absorption wall element adjacent to the first absorption wall element,
   the first absorption wall element and the second absorption wall element each include the absorption portions, and
   each of the absorption portions of the first absorption wall element is configured to support each of the absorption portions of the second absorption wall element.

9. The radiographic diagnosis apparatus according to claim 1, wherein
   two directions in which detection elements are able to be arranged in the X-ray detector are defined as a row direction and a channel direction,
   the absorption wall comprises absorption wall elements arranged along the channel direction, the absorption wall elements each extending in the row direction, and
   the absorption wall comprises absorption wall elements arranged along the row direction, the absorption wall elements each extending in the channel direction.

10. The radiographic diagnosis apparatus according to claim 9, wherein
    materials of the absorption wall elements arranged along the channel direction are changed along the channel direction and/or materials of the absorption wall elements arranged along the row direction are changed along the row direction.

11. The radiographic diagnosis apparatus according to claim 9, wherein
    the absorption wall elements, each extending in the row direction, have each a configuration in which an order of each of the absorption portions and a non-absorption portions is alternated along the row direction, and
    the absorption wall elements, each extending in the channel direction, have each a configuration in which an order of each of the absorption portions and a non-absorption portions is alternated along the channel direction.

12. The radiographic diagnosis apparatus according to claim 11, wherein
    the absorption wall includes a first absorption wall element and a second absorption wall element adjacent to the first absorption wall element,
    the first absorption wall element and the second absorption wall element each include the absorption portions, and
    each of the absorption portions of the first absorption wall element is configured to support each of the absorption portions of the second absorption wall element.

13. The radiographic diagnosis apparatus according to claim 1, wherein
    materials of the absorption portions arranged along the X-ray incident direction are changed along the X-ray incident direction.

14. A radiographic diagnosis apparatus comprising:
    an X-ray source configured to generate an X-ray;
    an X-ray detector configured to detect the X-ray and to generate an electric signal according to the X-ray; and
    a collimator provided on an X-ray incident side of the X-ray detector and the collimator including an absorption wall configured to absorb a scattered X-ray, the absorption wall including absorption portions arranged along an incident direction of the X-ray, wherein
    two directions in which detection elements are able to be arranged in the X-ray detector being defined as a row direction and a channel direction,
    the absorption wall has a configuration in which an order of each of the absorption portions and a non-absorption portions is alternated along the row direction when extending in the row direction, and the absorption wall has a configuration in which an order of each of the absorption portions and a non-absorption portions is alternated along the channel direction when extending in the channel direction.

15. A radiographic diagnosis apparatus comprising:
an X-ray source configured to generate an X-ray;
an X-ray detector configured to detect the X-ray and to generate an electric signal according to the X-ray;
a collimator provided on an X-ray incident side of the X-ray detector and the collimator including an absorption wall configured to absorb a scattered X-ray, the absorption wall including absorption portions arranged along an incident direction of the X-ray; and
a thinner absorption portion which is thinner than the absorption portions, the thinner portion being the same material as the absorption portions and being arranged between the absorption portions.

16. A radiation detector comprising a collimator equipped with an absorption wall configured to absorb a scattered X-ray, wherein
the absorption wall of the collimator includes absorption portions arranged along an incident direction of an X-ray from an X-ray source, and
the absorption portions are arranged at unequal intervals along the incident direction.

17. The radiation detector according to claim 16, wherein the absorption portions are disposed in such a manner that a number of absorption portions is sparse on a side close to the X-ray source in the incident direction as compared with a side close to an X-ray detector.

18. The collimator according to claim 16, wherein the absorption portions are disposed in such a manner that a number of absorption portions is sparse on a side close to the X-ray source in the incident direction as compared with a side close to an X-ray detector.

19. A collimator comprising an absorption wall configured to absorb a scattered X-ray, wherein
the absorption wall includes absorption portions arranged along an incident direction of an X-ray from an X-ray source, and
the absorption portions are arranged at unequal intervals along the incident direction.

* * * * *